(12) United States Patent
Bachman

(10) Patent No.: US 11,903,796 B1
(45) Date of Patent: Feb. 20, 2024

(54) BANDAGE FOR PEDIATRIC ANALGESIA

(71) Applicant: Christian G. Bachman, Century, FL (US)

(72) Inventor: Christian G. Bachman, Century, FL (US)

( * ) Notice: Subject to any disclaimer, the term of this patent is extended or adjusted under 35 U.S.C. 154(b) by 155 days.

(21) Appl. No.: 17/524,719

(22) Filed: Nov. 11, 2021

(51) Int. Cl.
*A61F 13/00* (2006.01)

(52) U.S. Cl.
CPC ............ *A61F 13/00051* (2013.01); *A61F 2013/0028* (2013.01); *A61F 2013/00102* (2013.01); *A61F 2013/00127* (2013.01)

(58) Field of Classification Search
CPC .. A61H 39/04; A61H 2201/10; A61H 39/002; A61H 2201/0207; A61H 2201/165; A61H 2201/1695; A61H 2205/04; A61H 2205/081; A61H 23/02; A61H 39/00; A61H 2201/1253; A61H 39/06; A61H 2205/125; A61H 2201/5097; A61H 7/001; A61H 2205/12; A61H 2201/0228; A61H 2201/5005; A61H 2201/1284; A61H 2201/0149; A61H 1/00; A61H 2201/1215; A61H 2201/5038; A61H 39/08; A61H 2201/0153; A61H 2201/164; A61H 39/086; A61H 2203/0456; A61H 2201/0157; A61H 23/0254; A61H 2201/0192; A61H 2205/02; A61H 9/0078; A61H 11/00; A61H 2201/0134; A61H 1/008; A61H 15/00; A61H 2201/1207; A61H 2201/5007; A61H 2201/50; A61H 23/0263; A61H 2201/169; A61H 2201/5002; A61H 7/007; A61H 2015/0014; A61H 2201/1654;
(Continued)

(56) References Cited

U.S. PATENT DOCUMENTS

| 5,470,304 A | * | 11/1995 | Decanto | ............... A61H 7/001 601/134 |
| 7,763,046 B2 | * | 7/2010 | Schouten | ............... A61H 39/04 606/204 |
| 2017/0319431 A1 | * | 11/2017 | Lee | ........................ A61H 39/04 |

FOREIGN PATENT DOCUMENTS

| KR | 20140128916 A | * | 11/2014 | |
| WO | WO-0141696 A1 | * | 6/2001 | ........... A61H 39/002 |
| WO | WO-2016206612 A1 | * | 12/2016 | ............. A61F 13/00 |

OTHER PUBLICATIONS

WO-0141696 Translation (Year: 2001).*
KR-20140128916 Translation (Year: 2014).*
WO-2016206612 Translation (Year: 2016).*

* cited by examiner

Primary Examiner — Kim M Lewis
(74) Attorney, Agent, or Firm — QuickPatents; Kevin Prince

(57) ABSTRACT

A bandage has a plurality of prongs extending from a portion of a bottom side of the bandage base. A depression region can be formed on the top side of the bandage base, opposite the plurality of prongs, where depressing the depression region can cause the prongs to interact with the user's skin, typically at a wound site. The depression region can be a raised dome having a button in a center region thereof, wherein depressing the raised dome beyond a given depth causes the raised dome to press the plurality of prongs against the skin of the user and automatically move back to its undepressed configuration. The prongs can have sufficient sharpness to create a slightly unpleasant sensation but can be dull enough not to create any damage to skin. Such counter irritation can provide an analgesic effect for the user.

19 Claims, 6 Drawing Sheets

(58) Field of Classification Search
CPC ........ A61H 2201/1609; A61H 15/0092; A61H 2201/01; A61H 2201/105; A61H 2201/1238; A61H 2205/062; A61H 2205/083; A61H 2201/0214; A61H 7/00; A61H 7/004; A61H 2201/1685; A61H 2201/5035; A61H 2205/10; A61H 1/0292; A61H 2201/1628; A61H 39/007; A61H 15/0078; A61H 2201/5071; A61H 2205/106; A61H 1/0296; A61H 2015/0042; A61H 2201/1604; A61H 39/02; A61H 2201/0165; A61H 2201/0257; A61H 2201/1607; A61H 2201/1669; A61H 9/005; A61H 9/0057; A61H 1/005; A61H 1/0218; A61H 2039/005; A61H 2201/0119; A61H 2201/1664; A61H 2201/5043; A61H 2205/065; A61H 7/003; A61H 2201/1481; A61H 2205/088; A61H 1/02; A61H 2201/0103; A61H 2201/0146; A61H 2201/1623; A61H 2201/1635; A61H 2201/5058; A61H 2230/50; A61H 2201/5048; A61H 23/00; A61H 23/0245; A61H 15/02; A61H 2201/0169; A61H 2201/168; A61H 2201/5023; A61H 2203/0406; A61H 2205/025; A61H 2205/027; A61H 2205/06; A61H 23/06; A61H 2015/0064; A61H 2201/1418; A61H 2203/0431; A61H 2205/024; A61H 2205/087; A61H 2201/0138; A61H 2201/0235; A61H 2201/1261; A61H 2201/149; A61H 2201/1642; A61H 2201/5064; A61H 2201/5082; A61H 2205/086; A61H 2205/108; A61H 23/006; A61H 35/006; A61H 2001/0233; A61H 2015/0021; A61H 2201/013; A61H 2201/0173; A61H 2201/1409; A61H 2201/1645; A61H 2201/5025; A61H 2201/5046; A61H 2201/5084; A61H 2203/03; A61H 2205/022; A61H 2205/08; A61H 23/0218; A61H 9/0092; A61H 15/0085; A61H 2023/0227; A61H 2201/0142; A61H 2201/025; A61H 2201/1454; A61H 2201/5056; A61H 2230/06; A61H 2230/80; A61H 7/008; A61H 1/0222; A61H 1/0229; A61H 2015/0035; A61H 2201/0184; A61H 2201/0188; A61H 2201/0278; A61H 2201/102; A61H 2203/00; A61H 2230/65; A61H 2230/82; A61H 7/002; A61H 9/00; A61H 1/0266; A61H 13/00; A61H 19/44; A61H 2015/0007; A61H 2015/0028; A61H 2201/0285; A61H 2201/163; A61H 2201/1652; A61H 2201/1671; A61H 2201/1676; A61H 2201/501; A61H 2203/0468; A61H 2205/021; A61H 2205/067; A61H 2205/085; A61H 23/04; A61H 33/6089; A61H 37/00; A61H 5/00; A61H 9/0007; A61H 9/0071; A61H 1/006; A61H 19/00; A61H 19/30; A61H 2015/005; A61H 2033/061; A61H 2201/0107; A61H 2201/0161; A61H 2201/0176; A61H 2201/1602; A61H 2201/1692; A61H 2201/5061; A61H 2230/255; A61H 2230/505; A61H 23/004; A61H 33/0087; A61H 33/066; A61H 7/006; A61H 2001/0207; A61H 2007/009; A61H 2009/0035; A61H 2011/005; A61H 2015/0071; A61H 2033/0054; A61H 2033/0079; A61H 2033/141; A61H 21/00; A61H 2201/0111; A61H 2201/0115; A61H 2201/0126; A61H 2201/0221; A61H 2201/1614; A61H 2201/1633; A61H 2201/1638; A61H 2201/1657; A61H 2201/1678; A61H 2201/5028; A61H 2201/5041; A61H 2201/5092; A61H 2203/0481; A61H 2205/00; A61H 2205/082; A61H 2205/084; A61H 2205/102; A61H 2230/04; A61H 2230/065; A61H 2230/25; A61H 2230/305; A61H 2230/425; A61H 2230/625; A61H 2230/855; A61H 23/0236; A61H 33/02; A61H 33/06; A61H 33/063; A61H 33/14; A61H 33/60; A61H 33/6057; A61H 39/083; A61H 1/001; A61H 1/003; A61H 1/0237; A61H 1/024; A61H 1/0244; A61H 1/0281; A61H 11/02; A61H 19/32; A61H 19/34; A61H 2001/0203; A61H 2001/0248; A61H 2015/0057; A61H 2023/002; A61H 2031/002; A61H 2033/0037; A61H 2033/0058; A61H 2033/022; A61H 2033/041; A61H 2033/068; A61H 2033/143; A61H 2033/145; A61H 2201/018; A61H 2201/0196; A61H 2201/0292; A61H 2201/1223; A61H 2201/1246; A61H 2201/1269; A61H 2201/14; A61H 2201/1463; A61H 2201/16; A61H 2201/1611; A61H 2201/1626; A61H 2201/1647; A61H 2201/1673; A61H 2201/1697; A61H 2201/5015; A61H 2201/5079; A61F 7/007; A61F 5/0111; A61F 5/30; A61F 5/028; A61F 5/14; A61F 13/00; A61F 13/02; A61F 5/0104; A61F 7/02; A61F 2013/00463; A61F 7/034; A61F 7/08; A61F 13/0243; A61F 2013/0028; A61F 5/0026; A61F 9/04; A61F 2007/0022; A61F 2007/0045; A61F 13/00063; A61F 2013/00468; A61F 5/0102; A61F 5/03; A61F 13/023; A61F 2007/0098; A61F 2007/026; A61F 2013/00106; A61F 2013/00472; A61F 2013/00919; A61F 13/00987; A61F 13/15; A61F 2007/0071; A61F 2007/0228; A61F 5/019; A61F 5/024; A61F 7/00; A61F 13/00051; A61F 2007/003; A61F 2007/0088; A61F 2007/0096; A61F 5/042; A61F 5/56; A61F 13/067; A61F 13/148; A61F 2007/0002; A61F 13/00012; A61F 13/00034; A61F 13/0233; A61F 2007/0077; A61F 2007/0226; A61F 2013/00285; A61F 2013/00314; A61F 2013/00497; A61F 2013/00604; A61F 2013/00655; A61F 5/34; A61F 5/40; A61F 7/03; A61F 11/14; A61F 11/145; A61F 13/064; A61F 13/08; A61F 2005/563; A61F 2007/0086; A61F 2013/0091; A61F 5/566; A61F 13/00059; A61F 13/00995; A61F 13/0203; A61F 13/0246; A61F 13/061; A61F 13/15203; A61F 2007/0054; A61F 2007/0087; A61F 2007/0093; A61F 2007/0095; A61F 2007/0244; A61F 2013/00119; A61F 2013/00123; A61F 2013/00127; A61F 2013/00153; A61F 2013/00182; A61F 2013/0037; A61F 2013/00536; A61F 2013/0054; A61F 2013/00931; A61F 2013/00936; A61F 5/026; A61F 7/0097; A61F 7/032; A61F 13/0206; A61F 13/0273; A61F 13/041; A61F 13/048; A61F 13/062; A61F 13/104; A61F 13/122; A61F 13/128; A61F 2/4644; A61F 2005/0167; A61F 2007/0039; A61F 2007/0048; A61F 2007/0231; A61F 2007/0246; A61F 2013/00387; A61F 2013/00489; A61F 2013/00553; A61F 2013/00902; A61F 2210/0095; A61F 5/01; A61F 5/0118; A61F 5/0585; A61F 5/32; A61F 5/41; A61F 7/10; A61F 9/027; A61F 13/0008; A61F 13/0213; A61F 13/0226; A61F 13/0253; A61F 13/101; A61F 13/102; A61F 13/105; A61F 13/107; A61F 13/108; A61F 13/124; A61F 13/14; A61F 13/475; A61F 13/4753; A61F 13/622; A61F 13/8405; A61F 15/002; A61F 2/02; A61F 2/954; A61F 2007/0004; A61F 2007/0005; A61F 2007/0009; A61F 2007/0011; A61F 2007/0024; A61F 2007/0036; A61F 2007/0047; A61F 2007/0056; A61F 2007/0073; A61F 2007/0078; A61F 2007/0204; A61F 2007/0207; A61F 2007/0233; A61F 2007/0266; A61F 2007/0268; A61F 2007/0295; A61F 2007/0296; A61F 2007/038; A61F 2013/00093; A61F 2013/00187; A61F 2013/00238; A61F 2013/00327; A61F 2013/00855; A61F 2013/00914; A61F 2013/0296; A61F 2013/8497; A61F 5/0096; A61F 5/0109; A61F 5/0195

USPC .......................................................... 606/204

See application file for complete search history.

BANDAGE FOR PEDIATRIC ANALGESIA

CROSS-REFERENCE TO RELATED APPLICATIONS

Not Applicable.

STATEMENT REGARDING FEDERALLY SPONSORED RESEARCH AND DEVELOPMENT

Not Applicable.

FIELD OF THE INVENTION

This invention relates to bandages, and more particularly to a bandage having a counter irritant for reducing the pain of minor injuries, especially in the pediatric population.

BACKGROUND

A counter irritant is described as "something such as heat or an ointment that is used to produce surface irritation of the skin, thereby counteracting underlying pain or discomfort". Many of these modalities are used in ordinary day-to-day life. Heat and cold and sometimes chemicals such as menthol etc. in various products serve this function. Indeed, even electrical stimulation as a counter irritant is well known and is most likely the underlying principle behind the transcutaneous electrical nerve stimulation (TENS) unit. Simple mechanical counter irritants can be seen in the human instinct to scratch or in holding or massaging a wounded appendage.

Bandages are often used to cover skin wounds. Typically bandages offer a padded and/or absorbent material that covers and protects the wound. If a user desires a counter irritant, the bandage must be removed to scratch or rub the wound area, for example.

Therefore, there is a need for a device that can both cover and protect a wound while allowing a user to apply a counter irritant stimulation to the wound to aid in pain management. The present invention accomplishes these objectives.

SUMMARY OF THE INVENTION

The present device is bandage that includes a bandage base having a top side and a bottom side, with the bottom side operable to be secured to skin of a user. A plurality of prongs can extend from a portion of the bottom side of the bandage base and a depression region can be disposed on a top side of the bandage base, opposite the plurality of prongs. A user, depressing the depression region, can move the plurality of prongs against the skin of the user. The depression region may be a collapsible dome-like structure so that it gives way and provides a quick, temporary push against the skin and then retracts back into the original orientation.

Further, when the dome is pressed, its collapsing function can produce an unpredictable element to the timing and intensity of the stimulus felt by the user, thus providing an increased analgesic efficacy. This unexpected dimension to the timing and intensity of the counter irritation is similar to the difference between tickling yourself and someone else doing it—if a sensation is completely predictable and expected. it ceases to be distracting. Conversely, if there is an unexpected and sudden aspect, it is more distracting. Without subscribing to any particular theory of operation, in some embodiments, this distraction can maximize pain relief. Additionally, there can be a further advantage of a placebo dimension given the novelty of the "button".

The analgesic bandage does not rely on chemicals but uses a mechanical counter irritant to achieve its goal. Further, the analgesic bandage, including the button/raised dome, can be colored and shaped to be child-friendly, such as including a favorite character shape, urging a child to use the counter irritant to help relieve pain during healing of their wound. Other features and advantages of the present invention will become apparent from the following more detailed description, taken in conjunction with the accompanying drawings, which illustrate, by way of example, the principles of the invention.

DETAILED DESCRIPTION OF THE PREFERRED EMBODIMENT

Figure 1:
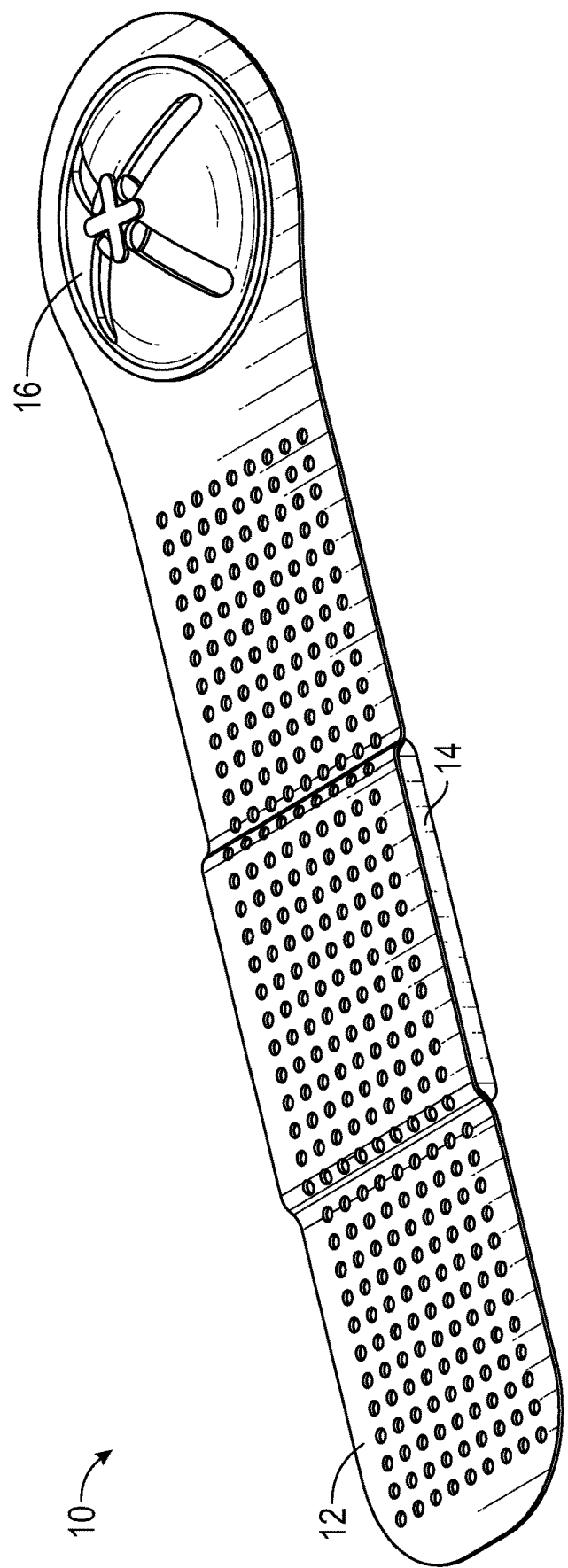
FIG. 1 is a top perspective view of a bandage according to an exemplary embodiment of the present invention.
Figure 2:
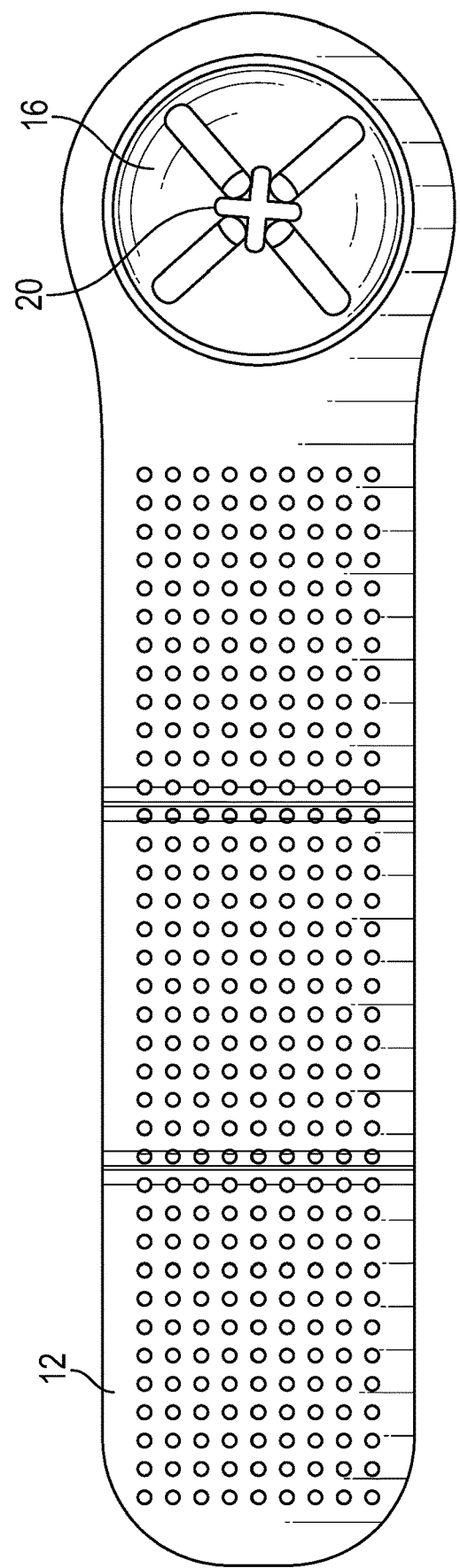
FIG. 2 is a top view of the bandage of FIG. 1.
Figure 3:
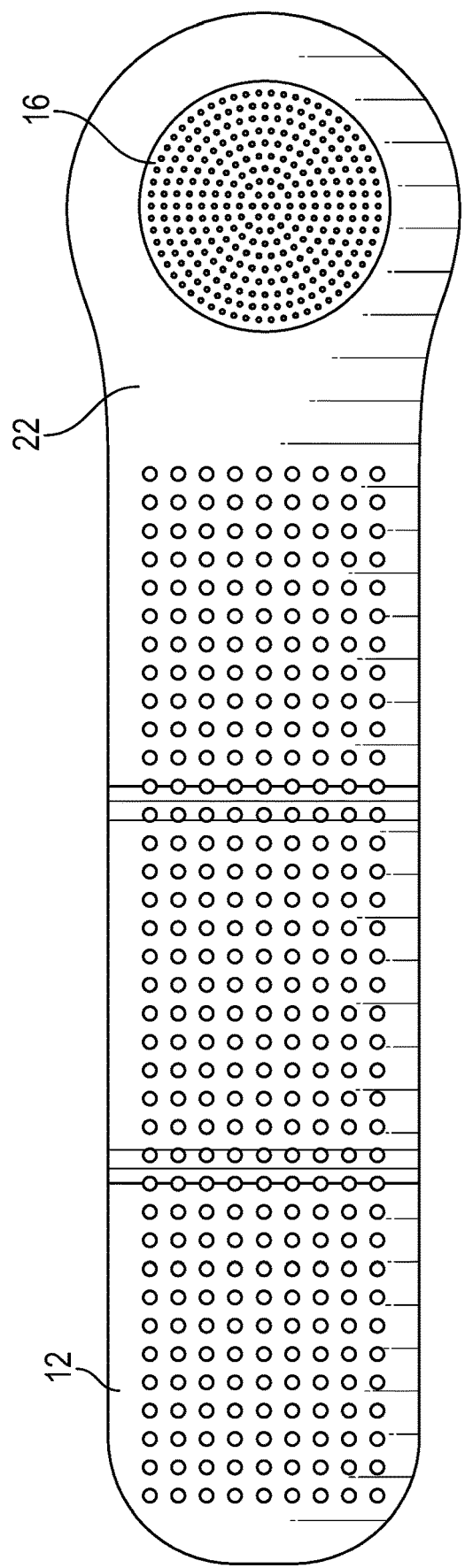
FIG. 3 is a bottom view of the bandage of FIG. 1.
Figure 4:
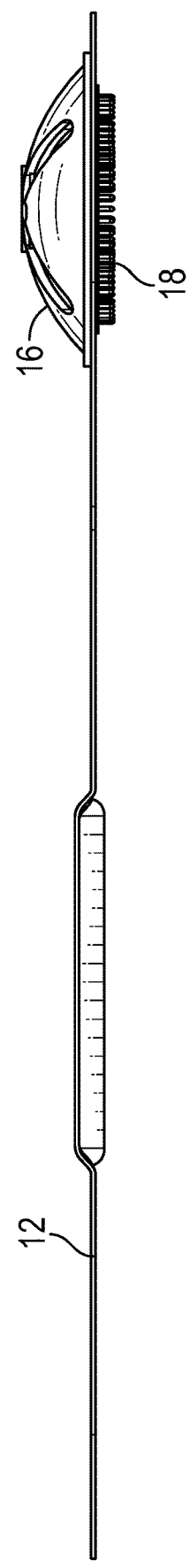
FIG. 4 is a side view of the bandage of FIG. 1.
Figure 5:
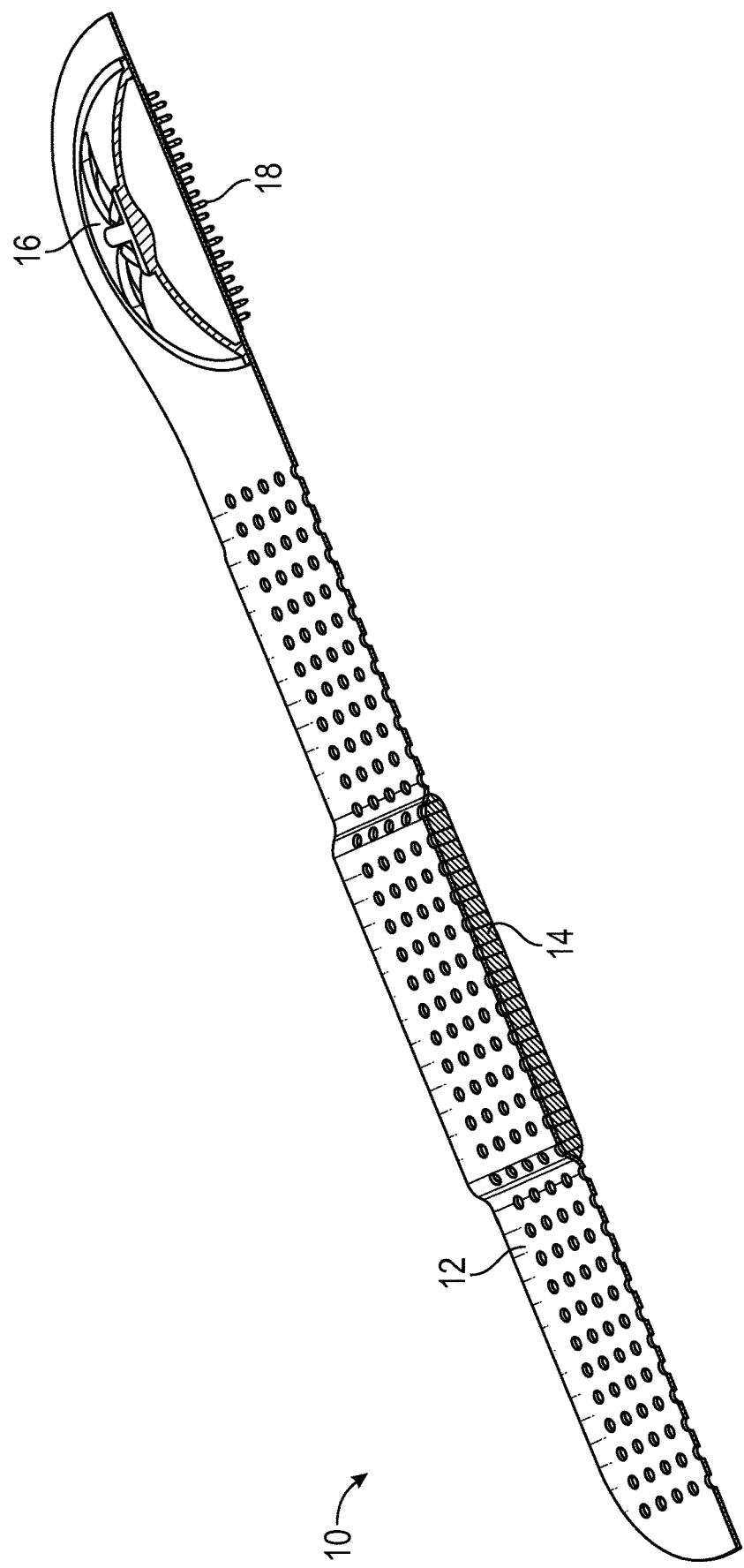
FIG. 5 is a length-wise cross-sectional view of the bandage of FIG. 1.
Figure 6:
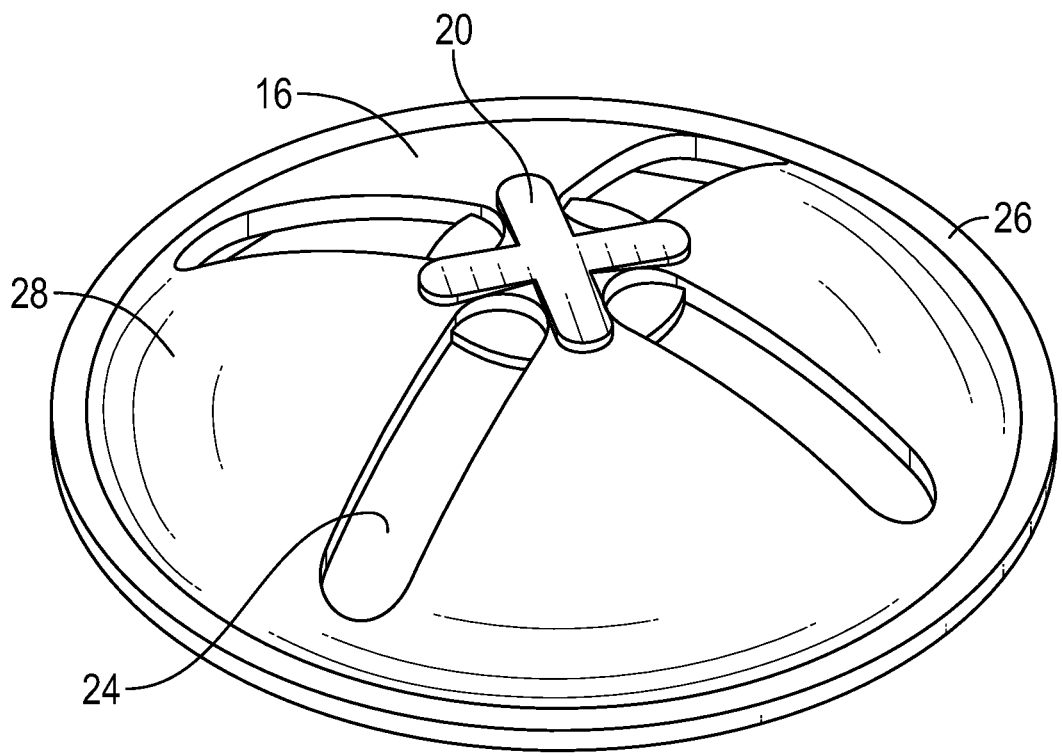
FIG. 6 is a close-up perspective view of the raised dome member of the bandage of FIG. 1.
Figure 7:
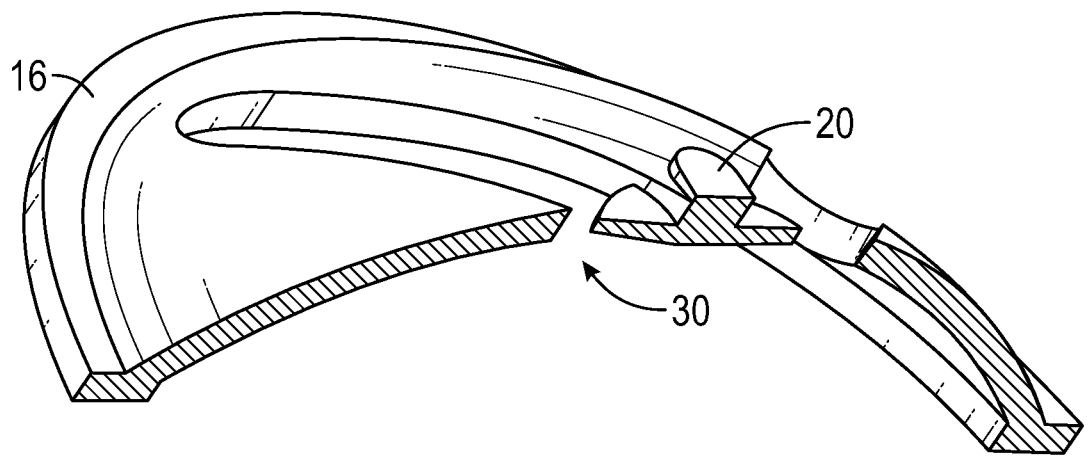
FIG. 7 is a cross-sectional view of the raised come member of the bandage of FIG. 1.
Figure 8:
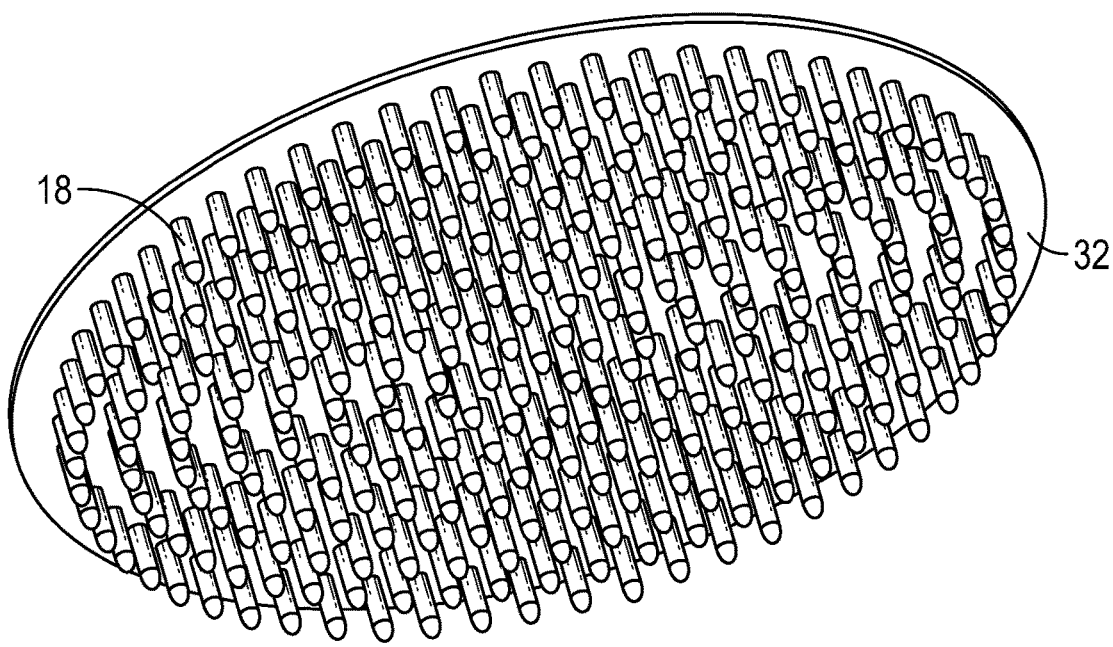
FIG. 8 is a close-up bottom perspective view of the region of the bandage of FIG. 1 positioned below the raised dome of FIG. 6.

Illustrative embodiments of the invention are described below. The following explanation provides specific details for a thorough understanding of and enabling description for these embodiments. One skilled in the art will understand that the invention may be practiced without such details. In other instances, well-known structures and functions have not been shown or described in detail to avoid unnecessarily obscuring the description of the embodiments.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively. Additionally, the words "herein," "above," "below" and words of similar import, when used in this application, shall refer to this application as a whole and not to any particular portions of this application. When the claims use the word "or" in reference to a list of two or more items, that word covers all of the following interpretations of the word: any of the items in the list, all of the items in the list and any combination of the items in the list. When the word "each" is used to refer to an element that was previously introduced as being at least one in number, the word "each" does not necessarily imply a plurality of the elements but can also mean a singular element.

Broadly, embodiments of the present invention provide a bandage having a plurality of prongs extending from a portion of a bottom side of the bandage base. A depression region can be formed on the top side of the bandage base, opposite the plurality of prongs, where depressing the depression region can cause the prongs to interact with the user's skin, typically at a wound site. The depression region can be a raised dome having a button in a center region thereof, wherein depressing the raised dome beyond a given depth causes the raised dome to press the plurality of prongs against the skin of the user and automatically move back to its undepressed configuration. The prongs can have sufficient sharpness to create a slightly unpleasant sensation but can be dull enough not to create any damage to skin. Such counter irritation can provide an analgesic effect for the user.

Referring to FIGS. 1 through 8, a bandage 10 can include a bandage base 12 having a top side and a bottom side, where the bottom side operable to be secured to the skin of a user. For example, an adhesive 22 may be applied to at least a portion of the back side of the bandage base. A plurality of prongs 18 can extend from a portion of the bottom side of the bandage base 12. This portion may be sized, for example, to correspond to a size of a wound site, however, where the portion having the prongs is smaller or larger than the wound site, an analgesic benefit may still be obtained. The plurality of prongs 18 may extend from a prong attachment portion 32 of the bandage base 12. The prong attachment portion 32 may be formed from the same material as the bandage base 12 or may be formed from a more rigid material such that depression a central region above the plurality of prongs on the top of the bandage can cause not only those prongs in the central region to be depressed, but, via the resiliency of the prong attachment portion 32, all of the plurality of prongs 32 may move generally uniformly downward toward the user's skin.

A depression region 16, 20 can be disposed on a top side of the bandage base, opposite the plurality of prongs 18. A user can depress the depression region to move the plurality of prongs against their skin. The bandage base may be made from typical bandage material, such as plastic, fabric, or the like. The prongs 18 may be made from rigid or semi-rigid plastic, metal or the like. Typically, the bandage base may be flexible to permit application of the bandage to various body parts. While one portion having a plurality of prongs is present, in some embodiments, more than one portion with prongs may be provided. Such a configuration can permit a user to feel the prickly sensation not only on their wound, but on unwounded skin, when desired, providing a further "distraction" from the pain of the wound.

In some embodiments, the depression region can be formed as a raised dome 16 having a button 20 in a center region thereof and a space 30 disposed thereunder. Depressing the raised dome 16 beyond a given depth causes the raised dome to press the plurality of prongs 18 against the skin of the user. In some embodiments, when the raised dome 18 gives way and presses on the plurality of prongs 18, the raised dome can automatically move back to its undepressed configuration. The raised dome 16 may be formed, for example, of a resilient plastic material.

In some embodiments, the raised dome 16 can include a plurality of side regions 28, extending from a base 26 of the raised dome 16, with a plurality of slots 24 separating the plurality of side regions 28. Such a configuration can be best envisioned in FIG. 6, for example.

In some embodiments, the bandage base can include an absorbent region 14 formed in an absorbent portion of the bottom side thereof. Such an absorbent region 14 may be formed from a material typically used in bandages, such as gauze, foam, or the like.

Figure 9:
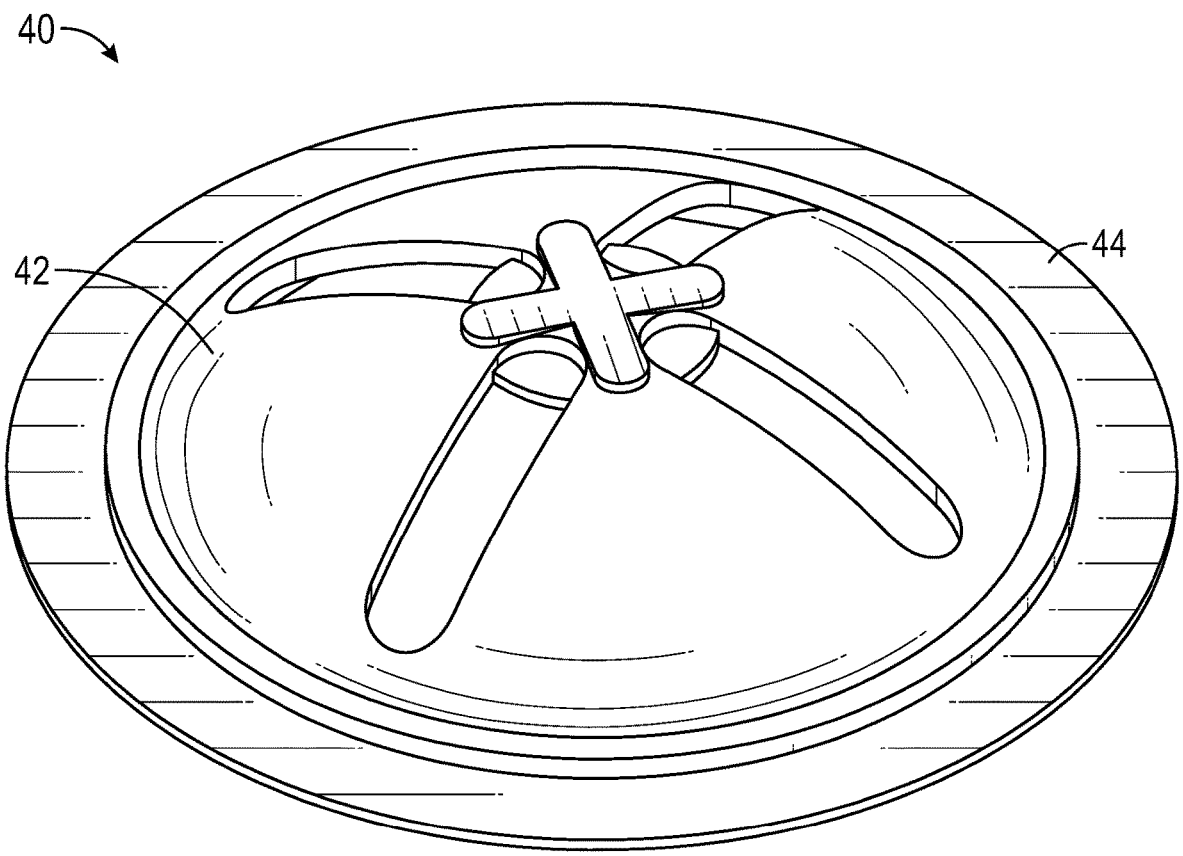
FIG. 9 is a perspective view of a bandage having an alternate bandage attachment region, according to an exemplary embodiment of the present invention.

In some embodiment, as shown in FIG. 1, for example, the bandage base is shaped as an elongated strap. In some embodiments, as shown in FIG. 9, a bandage 40 can include a bandage base 44 formed as in a patch shape, such as being a round shape surrounding the region having the plurality of prongs. Similar to the embodiment described above, a raised dome 42 may be provided to permit the user to articulate the prongs toward the user's skin.

While a particular form of the invention has been illustrated and described, it will be apparent that various modifications can be made without departing from the spirit and scope of the invention. For example, the plurality of prongs are shown as a circular region, however, such a region may be any geometric or non-geometric shape, such as rectangular, square, or the like. Further, the bandage base is shown as strap-like (FIG. 1) or round (FIG. 9), but other base shapes and sizes are contemplated within the scope of the present invention. Accordingly, it is not intended that the invention be limited, except as by the appended claims.

Particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific embodiments disclosed in the specification, unless the above Detailed Description section explicitly defines such terms. Accordingly, the actual scope of the invention encompasses not only the disclosed embodiments, but also all equivalent ways of practicing or implementing the invention.

The above detailed description of the embodiments of the invention is not intended to be exhaustive or to limit the invention to the precise form disclosed above or to the particular field of usage mentioned in this disclosure. While specific embodiments of, and examples for, the invention are described above for illustrative purposes, various equivalent modifications are possible within the scope of the invention, as those skilled in the relevant art will recognize. Also, the teachings of the invention provided herein can be applied to other systems, not necessarily the system described above. The elements and acts of the various embodiments described above can be combined to provide further embodiments.

All of the above patents and applications and other references, including any that may be listed in accompanying filing papers, are incorporated herein by reference. Aspects of the invention can be modified, if necessary, to employ the systems, functions, and concepts of the various references described above to provide yet further embodiments of the invention.

Changes can be made to the invention in light of the above "Detailed Description." While the above description details certain embodiments of the invention and describes the best mode contemplated, no matter how detailed the above appears in text, the invention can be practiced in many ways. Therefore, implementation details may vary considerably while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated.

While certain aspects of the invention are presented below in certain claim forms, the inventor contemplates the various aspects of the invention in any number of claim forms. Accordingly, the inventor reserves the right to add additional claims after filing the application to pursue such additional claim forms for other aspects of the invention.

What is claimed is:

1. A bandage comprising:
   a bandage base having a top side and a bottom side, the bottom side operable to be secured to skin of a user;
   a plurality of prongs extending from a portion of the bottom side of the bandage base;
   a depression region disposed on a top side of the bandage base, opposite the plurality of prongs, the depression region being formed as a raised dome having a button in a center region thereof;
   wherein depressing the raised dome beyond a given depth causes the raised dome to press the plurality of prongs against the skin of the user and automatically move back to its undepressed configuration.

2. The bandage of claim 1, wherein the raised dome includes a plurality of side regions extending from a base of the raised dome with a plurality of slots separating the plurality of side regions.

3. The bandage of claim 1, further comprising an adhesive disposed on at least an adhesive portion of the bottom side of the bandage base.

4. The bandage of claim 1, wherein the bandage base is shaped as an elongated strap.

5. The bandage of claim 4, wherein the bandage base includes an absorbent region formed in an absorbent portion of the bottom side thereof.

6. The bandage of claim 1, wherein the bandage base is formed as in a round shape.

7. The bandage of claim 1, where in the plurality of prongs are configured to apply a pressure against the skin of the user without damaging the skin.

8. A bandage comprising:
   a bandage base having a top side and a bottom side;
   a plurality of prongs extending from a portion of the bottom side of the bandage base;
   a raised dome disposed opposite the plurality of prongs, wherein depressing the raised dome beyond a given depth causes the raised dome to press the plurality of prongs against the skin of the user and automatically move back to its undepressed configuration; and
   an adhesive on an adhesive portion of the bottom side of the bandage base.

9. The bandage of claim 8, wherein the raised dome includes a plurality of side regions extending from a base of the raised dome with a plurality of slots separating the plurality of side regions.

10. The bandage of claim 8, wherein the bandage base is shaped as an elongated strap.

11. The bandage of claim 10, wherein the bandage base includes an absorbent region formed in an absorbent portion of the bottom side thereof.

12. The bandage of claim 8, wherein the bandage base is formed as in a round shape.

13. The bandage of claim 8, where in the plurality of prongs are configured to apply a pressure against the skin of the user without damaging the skin.

14. A method of decreasing pain associated with a wound of skin of a user, comprising:
    applying the bandage of claim 8 to the user with the plurality of prongs disposed adjacent the wound;
    depressing the raised dome to cause the raised dome to press the plurality of prongs onto the wound; and
    releasing the raised dome to cause the raised dome to return to its undepressed position.

15. The method of claim 14, wherein the raised dome includes a plurality of side regions extending from a base of the raised dome with a plurality of slots separating the plurality of side regions.

16. The method of claim 14, wherein the bandage base is shaped as an elongated strap.

17. The method of claim 16, further comprising disposing an absorbent region, formed in an absorbent portion of the bottom side of the bandage base, adjacent the wound.

18. The method of claim 14, wherein the bandage base is formed as in a round shape.

19. The method of claim 14, where in the plurality of prongs apply a pressure against the wound without damaging the skin.

* * * * *